United States Patent
Frost et al.

(10) Patent No.: US 8,492,581 B2
(45) Date of Patent: Jul. 23, 2013

(54) SULFONATION OF POLYHYDROXYAROMATICS

(75) Inventors: John W Frost, Okemos, MI (US); Vu Bui, East Lansing, MI (US)

(73) Assignee: Amyris, Inc., Emeryville, CA (US)

( * ) Notice: Subject to any disclaimer, the term of this patent is extended or adjusted under 35 U.S.C. 154(b) by 348 days.

(21) Appl. No.: 12/859,922

(22) Filed: Aug. 20, 2010

(65) Prior Publication Data

US 2011/0046412 A1 Feb. 24, 2011

Related U.S. Application Data

(60) Provisional application No. 61/274,822, filed on Aug. 21, 2009.

(51) Int. Cl.
*C07C 309/00* (2006.01)
(52) U.S. Cl.
USPC .............................................. 562/99; 562/45
(58) Field of Classification Search
USPC ................................................... 562/45, 99
See application file for complete search history.

(56) References Cited

U.S. PATENT DOCUMENTS

| | | |
|---|---|---|
| 3,864,286 A | 2/1975 | Anderson |
| 4,358,410 A | 11/1982 | Demler et al. |
| 5,487,987 A | 1/1996 | Frost et al. |
| 5,616,496 A | 4/1997 | Frost et al. |
| 5,629,181 A | 5/1997 | Frost et al. |
| 6,472,109 B2 | 10/2002 | Frost |
| 2009/0176684 A1 | 7/2009 | Gardner et al. |

FOREIGN PATENT DOCUMENTS

| | | |
|---|---|---|
| WO | 2007144344 A1 | 12/2007 |
| WO | 2009/059254 | 5/2009 |

OTHER PUBLICATIONS

Veselinovic et al., J. of Applied Spectroscopy, vol. 62(6), pp. 1043-1046 (1995).

*Primary Examiner* — Porfirio Nazario Gonzalez
(74) *Attorney, Agent, or Firm* — Jennifer A. Camacho; Fang Xie; Greenberg Traurig, LLP

(57) ABSTRACT

The present invention provides improved process for the sulfonation of hydroxyaromatics amenable to direct isolation of the sulfonylated hydroxyaromatics in their free-acid forms. The process allows for the recyclization of sulfuric acid and minimizes waste. The starting materials are from a renewal resource, e.g., biomass, and contain detectable $^{14}C$ up to a $^{14}C$ content of 0.0000000001% (one part per trillion). The products made include sulfonated catechol, disulfonated pyrogallol and sulfonated protocatechuic acid.

17 Claims, No Drawings

SULFONATION OF POLYHYDROXYAROMATICS

CROSS REFERENCE TO RELATED APPLICATIONS

This application claims the benefit of priority from U.S. Provisional Patent Application No. 61/274,822, filed on 21 Aug. 2009, which is hereby incorporated by reference in its entirety.

FIELD OF THE INVENTION

The present invention provides an improved process for the sulfonation of hydroxyaromatics and products made by this process. The described process enables isolation of the sulfonylated hydroxyaromatcs in their free acid forms, which avoids generation of salts as waste products and facilitates recycling of sulfuric acid. The described process also enables sulfonylated hydroxyaromatics to be made from renewable carbon atoms derived from biomass.

BACKGROUND OF THE INVENTION

Tiron™ (trademark of E.I. du Pont de Nemours and Company) is a known chelant. However, it is currently too expensive to make for commercial purposes. For example, in published US 2009/0176684 detergent compositions containing catechols, such as Tiron™ (1,2-dihydroxybenzene-3,5-disulfonic acid), which do not have or do not develop the reddish color associated with the catechol/ferric iron chelate, are disclosed.

Several attempts have been made to prepare Tiron™ or its derivatives but for various reasons, none of these have been commercially practical or cost effective for this purpose. A few of these prior efforts are discussed below.

Some groups have attempted this process using catechol as the starting compound. Cousin, in *Compt. Rend.* 117, 113 (1893); *Bull. Soc. Chim.* 11, 103 (1894); and *Ann. Chim.* 13, 511 (1898), made the free sulfonic acid of Tiron™ using oleum (30%) at 100° C. This process required the use of oleum and elevated temperature. Jakob Pollak and Erich Gebauer-fulnegg, *Monatshefte fuer Chemie*, 47, 109 (1926) again made the free sulfonic acid of Tiron™ using ClSO$_3$H at RT. This process required the use of a chlorinated reagent.

Rhodia in WO 2007/144344 A1, published 21 Dec. 2007, heated a reaction mixture of catechol in H$_2$SO$_4$ to 85-90° C. to form (Tiron™) disodium salt. However, the free acid of 4,5-dihydroxy-1,3-benzenedisulfonic acid (Tiron™) does not precipitate from the sulfuric acid reaction mixture and neutralization is required in order to precipitate the sodium salt of Tiron™. This leads to a substantial salt waste stream and complicates the task of recycling the H$_2$SO$_4$.

A compound similar to Tiron™, namely a 2,3,4-trihydroxybenzenesulfonic acid, has been made starting with 1,2,3-trihydroxybenzene, which is also known as pyrogallol (PG). The process by Schieff, *Ann.* 178, 187 (1875) used H$_2$S$_2$O$_7$ at 100° C. This process required the use of pyrosulfuric acid and elevated temperature. Two groups, Delage, *Compt. Rend.* 131, 450 (1900); 133, 298 (1901); 136, 760, 893, 1202 (1903) and Anschutz, *Ann.* 415, 87 (1918), tried this process using H$_2$SO$_4$ at 100° C. These processes required elevated temperature and produced a mixture of products.

Two groups, Delage, *Compt. Rend.* 132, 421 (1901); and Pollak, Gebauer-fulnegg, and Litvay, *Monatshefte fuer Chemie*, 47, 537 (1927), used PG as the starting material to make 4,5,6-trihydroxy-1,3-benzenedisulfonic acid, using H$_2$SO$_4$ at 100° C. This process required elevated temperature.

Clearly, it would be advantageous to have a cost effective and practical approach using renewable biomass resources to make such additives.

BRIEF SUMMARY OF THE INVENTION

The present invention provides a novel process using renewable carbon atoms derived from biomass containing detectable $^{14}$C content determined according to ASTM D6866-08 and preferably containing a $^{14}$C content up to 0.0000000001% (one part per trillion) to make sulfonated hydroxyaromatic compounds. Specifically, this invention provides a process for preparing a sulfonylated hydroxyaromatic compound of the formula:

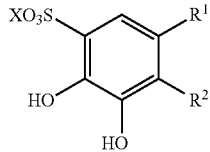

Formula I wherein: X is H or Na; R$^1$ is SO$_3$H, SO$_3$Na, CO$_2$H, or CO$_2$Na; and R$^2$ is H or OH; which comprises reacting a compound derived from renewable carbon sources containing up to 1 part per trillion of $^{14}$C of the formula:

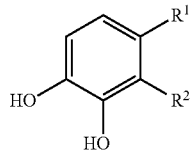

Formula II wherein: R$^1$ is H or CO$_2$H; and R$^2$ is H or OH; with concentrated sulfuric acid at a temperature from room temperature (RT) to about 120° C. and, optionally under a N$_2$ atmosphere; and with separation of the product based on precipitation of the free acid of the sulfonylated hydroxyaromatic, optionally in the presence of a solvent. The compounds of Formula I having renewable carbon atoms derived from biomass containing detectable $^{14}$C content determined according to ASTM D6866-08 and preferably containing a $^{14}$C content up to 0.0000000001% (one part per trillion) are also novel.

DETAILED DESCRIPTION OF THE INVENTION

It is understood that the terminology used herein is for the purpose of describing particular embodiments only and is not intended to be limiting. As used in this specification, the singular forms "a", "an", and "the" include plural referents unless the content clearly indicates otherwise.

Also, certain US patents and PCT published applications have been incorporated by reference. However, the text of such patents is only incorporated by reference to the extent that no conflict exists between such text and other statements set forth herein. In the event of such conflict, then any such conflicting text in such incorporated by reference US patent or PCT application is specifically not so incorporated in this patent.

Glossary

The following terms as used in this application are to be defined as stated below and for these terms, the singular includes the plural.

biomass refers to the carbon atoms in the form of cellulose, lignocellulose, and hemicellulose and starch contained in nonfood and food plants such as corn, sweet sorghum and sugar cane and their waste which cannot be used as a food source which can be broken down to simple sugars which can be converted into the compounds of Formula II; such compounds containing detectable $^{14}C$ content determined according to ASTM D6866-08 and preferably contain a $^{14}C$ content up to 0.0000000001% (one part per trillion)

catechol means 1,2-dihydroxybenzene conc. means concentrated; for sulfuric acid means from about 50% to about 99%, preferably ~98% as purchased from Sigma Aldrich g means grams hr(s). means hour(s)

L means liter min(s) means minute(s)

mL means milliter

PCA means protocatechuic acid or 3,4-dihydroxybenzoic acid

PG means pyrogallol or 1,2,3-trihydroxybenzene

RBF means round bottom flask

RT means ambient temperature or room temperature, from about 20 to about 25° C.

SPCA means sulfonated protocatechuic acid or 3,4-dihydroxy-5-sulfobenzoic acid

Tiron™ means sulfonated catechol or 1,2-dihydroxy-3,5-benzenedisulfonate sodium salt General Remarks Because sulfonylated hydroxyaromatics are desired compounds to make several useful additives for example such as determining metal ion concentrations, serving as chelants and removing unwanted coloration in fabric care, many processes have been tried over the years to use various starting compounds to obtain them.

Many processes have started with catechol, but this compound has proven expensive as the source varies with supply and generally is either in short supply and/or high priced. Thus as a commercial resource it has not proven a good starting compound. For sustainability considerations and reduction of carbon footprints, there is also a desire to use starting materials derived from renewable feedstocks in the synthesis and manufacture of sulfonylated hydroxyaromatics.

Another starting compound used is pyrogallol (PG) but the reactions usually have a low yield, lead to product mixtures, or make an alkali metal salt product which can lead to undesirable salt waste streams or complicates recycling of the sulfonylation reagent. The process often requires high temperatures for a significant time, which adds to the cost of the final product.

In contrast to the known processes, the present invention provides a renewable starting material from biomass, using a process that can be run at RT or elevated temperature and high yield. Also with recyclization of the conc. sulfuric acid and lower waste stream issues this process is more environmentally acceptable. The following flow chart illustrates the present process in general terms.

Process Flow Chart

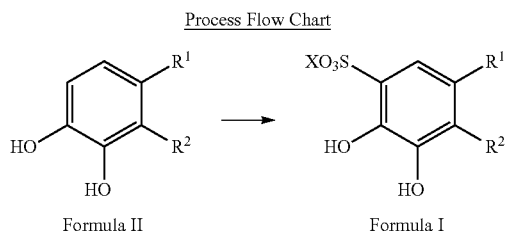

Formula II          Formula I

In Formula II, the starting compound has $R^1$ is H or $CO_2H$; and $R^2$ is H or OH. When $R^1$ and $R^2$ are both H, then the compound is catechol; when $R^1$ is H and $R^2$ is OH, then the starting compound is pyrogallol; and when $R^1$ is $CO_2H$ and $R^2$ is H, then the starting compound is protocatechuic acid. Because biomass is a starting source to make these compounds of Formula II, these compounds contain detectable $^{14}C$ up to a $^{14}C$ content of 0.0000000001% (one part per trillion). The sulfonation reaction uses conc. $H_2SO_4$, which can be recycled.

In Formula I, the product has $R^1$ is $SO_3H$ or $CO_2H$ and $R^2$ is H or OH. When $R^1$ is $SO_3H$ and $R^2$ is H, then the product is Tiron™. When $R^1$ is $SO_3H$ and $R^2$ is OH, then the product is 4,5,6-trihydroxy-1,3-benzenesulfonic acid. When $R^1$ is $CO_2Na$ and $R^2$ is H, then the product is 3,4-dihydroxy-5-sulfobenzoic acid also referred to as sulfonated protocatechuic acid (SPCA). Each of these compounds will contain detectable $^{14}C$ content up to a $^{14}C$ content of 0.0000000001% (one part per trillion) from the compounds of Formula II.

For the above general process of this invention the reaction conditions are: 1) use of concentrate sulfuric acid; 2) temperatures from RT to about 120° C.; 3) preferably under a $N_2$ atmosphere; and 4) time is not critical but should be for a time sufficient to allow the desired sulfonation to occur. Unlike prior processes no fuming sulfuric acid is used and the free acid of the sulfonylated hydroxyaromatic is isolated from the reaction mixture. The free acid usually precipitates easily and thereby reduces the waste stream issues while allowing the sulfuric acid to be recycled. Optionally, if needed to aid in separation of the compounds of Formula I an additional solvent can be present. Sulfonylation is possible from RT through elevated temperatures.

When catechol is used as the starting compound it has been found that concentrated sulfuric acid is the preferred sulfonation agent followed by neutralization with base such as sodium hydroxide. This synthetic route avoids the use of oleum or fuming sulfuric acid. However, neutralization of the sulfonylation reaction mixture is required in order to separate the sulfonylated hydroxyaromatic as its sodium salt.

If the starting compound is pyrogallol (PG), then the present process uses concentrated sulfuric acid as the preferred sulfonation agent. The sulfuric acid can be recycled.

One starting compound is protocatechuic acid (PCA), which is obtained from biomass by fermentation. No process for commercial production of PCA has been available previously in sufficient scale. Now PCA is obtained from microbial synthesis from glucose as the starting material derived from renewable starch or cellulose feedstocks [see W. Li et al., *J. Am. Chem. Soc.* 127 (9), 2874-2882 (2005); and Frost et al. U.S. Pat. No. 5,616,496, U.S. Pat. No. 5,629,181, and U.S. Pat. No. 5,487,987, each incorporated herein by reference]. The product obtained is SPCA, which precipitates from the reaction solution as the free acid. No neutralization is required and the product is free of alkali metal salts.

The compounds of Formula I have utility as chelants that can be used in a variety of ways, including but not limited to determining metal ion concentrations, serving as chelants and removing unwanted coloration in fabric care.

This invention will be further clarified by a consideration of the following examples, which are intended to be purely exemplary of the present invention. The lettered Examples are comparative. The numbered Examples are of this invention.

EXAMPLES

Example A

Procedure from WO 2007/144344 A1 by Rhodia

Into a 1 L flask containing 682 g of sulfuric acid was added 150 g of catechol at RT. The reaction mixture was heated to 85-90° C. for 5 h for the sulfonation process to occur. When the reaction mixture has cooled down to 50° C., 231.9 g of 47% NaOH solution was added to the reaction mixture and 1,2-dihydroxy-3,5-benzenedisulfonate sodium salt precipitated. The reaction mixture was cooled down to 15-25° C. and the solid was filtered through a Büchner funnel. The solid was washed (3×) with 115 g of isopropanol and dried under vacuum at 60° C. to provide 290 g of Tiron™ as an off-white solid in a yield of 68%. Thus this process requires neutralization with base and forms the salt.

Example B

Sulfonation of pyrogallol (PG) with $H_2SO_4$ at 90° C. for 5 h

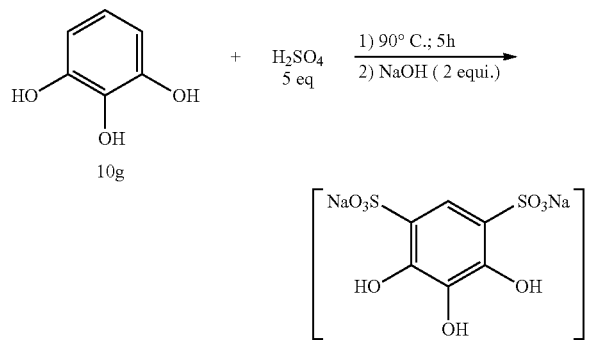

Into a RBF containing PG (10 g, 79.3 mmol), sulfuric acid (38.9 g, 396 mmol) was added. The mixture was heated at 90° C. in an oil bath for 5 h. The reaction was allowed to cool to 50° C. and aqueous NaOH (6.36 g in 20 mL water) was added dropwise to the reaction mixture and the resulting precipitate was obtained by filtration.

The $^1H$ NMR of the isolated solid has only one peak at 7.1 ppm; however, no carbon was detected by $^{13}C$ NMR, suggesting that the isolated solid might be of some inorganic salt. Thus this process as disclosed by Rhodia in the patent WO 2007/144344 A1 is not applicable for production of the desired 4,5,6-trihydroxy-1,3-benzenedisulfonic acid for further use.

Present invention using catechol derived from biomass as the starting compound.

Example 1

Sulfonation of Catechol in Concentrated $H_2SO_4$

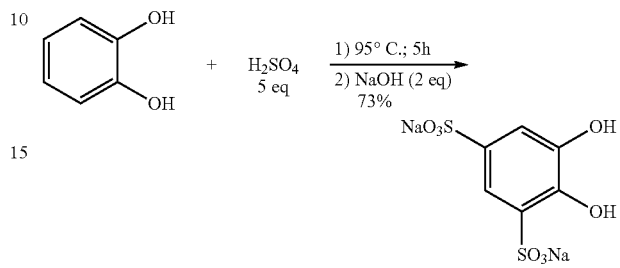

The sulfonation of catechol derived from biomass using concentrated sulfuric acid was followed as described in Example A with minor modifications.

Into a 1 L RBF containing 682 g of concentrated (98%) sulfuric acid, was added 150 g of catechol at RT. The mixture was heated at 95° C. for 5 h. When the reaction mixture was cooled to 50° C., 232 g of 47% (by weight) NaOH solution in water was added dropwise via an addition funnel to the reaction mixture to precipitate 1,2-dihydroxy-3,5-benzenedisulfonate sodium salt. Upon complete addition of NaOH solution, the reaction was cooled to 15-25° C. and the precipitate was filtered through a Büichner funnel. The solid was washed with isopropanol (600 mL) and dried under vacuum at 60° C. to yield 312 g (73% yield) of 1,2-dihydroxy-3,5-benzenedisulfonate sodium salt as an off-white solid.

Present invention using pyrogallol (PG) derived from biomass as the starting material.

Example 2

Sulfonation of pyrogallol (PG) with concentrated $H_2SO_4$ at RT

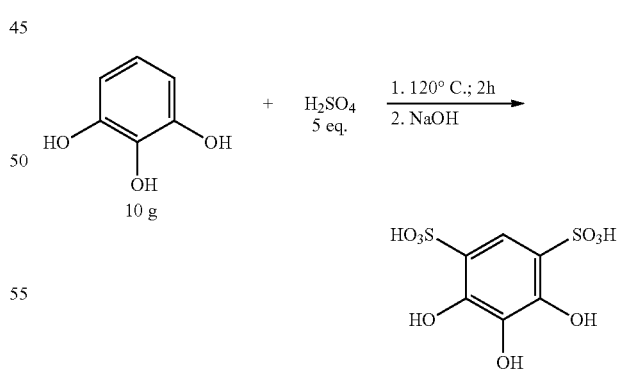

Into a round bottom flask containing PG (10 g, 79.3 mmol), sulfuric acid (38.9 g, 396 mmol) was added at room temperature under nitrogen atmosphere. With stirring, the mixture was allowed to react at RT for 24 h. 100 mL of acetonitrile was then added to the reaction flask and the resulting white precipitate was obtained by filtration. The white solid was washed with pentane (2×) and dried under reduced pressure to provide 3.6 g of 4,5,6-trihydroxy-1,3-benzenedisulfonic acid. The acetonitrile filtrate was cooled to 0° C. in an ice-water bath and this induced more precipitation that was filtered and dried to yield another 4.8 g of 4,5,6-trihydroxy-1,3-benzenedisulfonic acid in an overall yield of 37%.

$^1$H and $^{13}$C NMR analysis of the isolated free acid pyrogallol disulfonate formed from sulfonylation of pyrogallol are as follows:

$^1$H NMR (300 MHz, DMSO-$_{d6}$): ppm 7.1 (s).

$^{13}$C NMR (75 MHz, DMSO-$_{d6}$): ppm 115.6, 122.1, 132.5, 144.0.

Process of this invention using PCA derived from biomass as the starting compound to make SPAC.

Example 3

Sulfonation of Protocatechuic acid (PCA) with $H_2SO_4$ at 120° C.

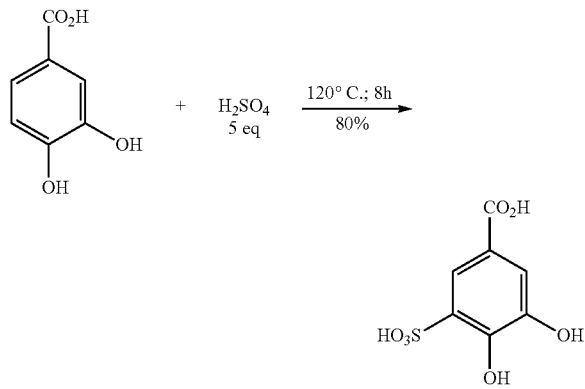

PCA (10 g, 65 mmol) was mixed with concentrated sulfuric acid (39 g, 398 mmol). The mixture was heated at 120° C. for 8 h. The reaction mixture was diluted with 100 mL acetonitrile resulting in the formation of a white precipitate, which was filtered, washed with excess acetonitrile, and dried under reduced pressure to yield 12.2 g (80% yield) of the free diacid of 3,4-dihydroxy-5-sulfobenzoic acid (SPCA).

The $^1$H and $^{13}$C NMRs of the isolated product confirmed its structure and its spectra are as follows:

$^1$H NMR (300 MHz, DMSO-$_{d6}$): ppm 7.2 (m, 1H), 7.5 (m, 1H).

$^{13}$C NMR (75 MHz, DMSO-$_{d6}$): ppm 117.0, 119.9, 120.7, 130.8, 145.7, 146.6, 167.1.

Elemental analysis for $C_7H_6O_7S$: C, 35.90; H, 2.58. Found: C, 35.59; H, 2.62.

Although the invention has been described with reference to its preferred embodiments, those of ordinary skill in the art may, upon reading and understanding this disclosure, appreciate changes and modifications which may be made which do not depart from the scope and spirit of the invention as described above or claimed hereafter. Accordingly, this description is to be construed as illustrative only and is for the purpose of teaching those skilled in the art the general manner of carrying out the invention.

What is claimed is:

1. A process for preparing a sulfonated hydroxyaromatic compound of formula I:

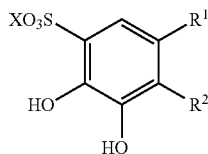

Formula I wherein: X is H or Na; $R^1$ is $SO_3H$, $SO_3Na$, $CO_2H$, or $CO_2Na$; and $R^2$ is H or OH;

said process comprising: reacting a compound of formula II derived from biomass:

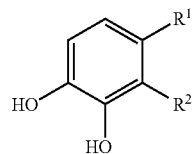

Formula II wherein: $R^1$ is H or $CO_2H$; and $R^2$ is H or OH; with concentrated sulfuric acid at a temperature from room temperature to about 120° C. to form the sulfonated hydroxyaromatic compound of Formula I; and separating the sulfonated hydroxyaromatic compound therefrom based on precipitation of the free acid of the sulfonated hydroxyaromatic compound.

2. The process of claim 1 wherein the reacting step is performed under a $N_2$ atmosphere.

3. The process of claim 1 wherein the separating step is performed in the presence of a solvent.

4. The process of claim 1 wherein in Formula I $R^1$ is $SO_3Na$ and $R^2$ is H, and the sulfonated hydroxyaromatic compound is sulfonated catechol; and wherein in Formula II $R^1$ and $R^2$ are both H, and the compound of Formula II is catechol.

5. The process of claim 1 wherein in Formula I $R^1$ is $SO_3Na$ and $R^2$ is OH, and the sulfonated hydroxyaromatic compound is disulfonated pyrogallol; and wherein in Formula II $R^1$ is H and $R^2$ is OH, and the compound of Formula II is pyrogallol.

6. The process of claim 1 wherein in Formula I $R^1$ is $CO_2Na$ and $R^2$ is H, and the sulfonated hydroxyaromatic compound is sulfonated protocatechuic acid; and wherein in Formula II $R^1$ is $CO_2H$ and $R^2$ is H, and the compound of Formula II is protocatechuic acid.

7. The process of claim 1 wherein the compound of Formula II is derived from biomass-derived renewable carbon atoms by fermentation methods.

8. A sulfonated hydroxyaromatic compound of formula I:

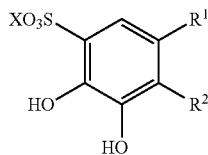

Formula I wherein: X is H or Na; $R^1$ is $SO_3H$, $SO_3Na$, $CO_2H$, or $CO_2Na$; and $R^2$ is H or OH;

and wherein all carbon atoms of said sulfonated hydroxyaromatic compound are derived from biomass.

9. The sulfonated hydroxyaromatic compound of claim 8 wherein X is H, $R^1$ is $CO_2H$ and $R^2$ is H, and the sulfonated hydroxyaromatic compound is 3,4-dihydroxy-5-sulfobenzoic acid.

10. A process for preparing a sulfonated hydroxyaromatic compound of formula I:

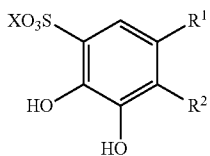

Formula I wherein: X is H or Na; $R^1$ is $SO_3H$, $SO_3Na$, $CO_2H$, or $CO_2Na$; and $R^2$ is H or OH;
said process comprising:
providing a compound of formula II derived from biomass:

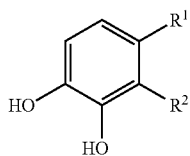

Formula II wherein $R^1$ is H or $CO_2H$, and $R^2$ is H or OH; and
reacting the compound of formula II with concentrated sulfuric acid at a temperature from room temperature to about 120° C. to form the sulfonated hydroxyaromatic compound of Formula I.

11. The process of claim 10 further comprising precipitating a free acid of said sulfonated hydroxyaromatic compound.

12. The process of claim 11 wherein the precipitating step is performed in the presence of a solvent.

13. The process of claim 10 wherein the reacting step is performed under a $N_2$ atmosphere.

14. The process of claim 10 wherein the sulfonated hydroxyaromatic compound of Formula I is sulfonated catechol; and the compound of Formula II is catechol.

15. The process of claim 10 the sulfonated hydroxyaromatic compound of Formula I is disulfonated pyrogallol; and the compound of Formula II is pyrogallol.

16. The process of claim 10 wherein the sulfonated hydroxyaromatic compound is sulfonated protocatechuic acid; and the compound of Formula II is protocatechuic acid.

17. The process of claim 1 wherein the compound of Formula II contains carbon atoms derived from biomass by fermentation.

* * * * *